(12) United States Patent
Yoshida et al.

(10) Patent No.: US 7,670,564 B2
(45) Date of Patent: Mar. 2, 2010

(54) LIQUID DISPENSING APPARATUS, AUTOMATIC ANALYZER USING SAME, AND LIQUID SURFACE DETECTING APPARATUS

(75) Inventors: Goro Yoshida, Hitachinaka (JP); Jun Maeda, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1281 days.

(21) Appl. No.: 11/044,593

(22) Filed: Jan. 28, 2005

(65) Prior Publication Data

US 2005/0242117 A1      Nov. 3, 2005

(30) Foreign Application Priority Data

Feb. 6, 2004     (JP)     ............... 2004-030042

(51) Int. Cl.
    *G05D 9/00*     (2006.01)
(52) U.S. Cl. .............. 422/106; 422/105; 422/100; 222/113; 73/427
(58) Field of Classification Search .......... 422/100, 422/103, 105, 106, 63–68.1; 222/113; 73/290 R, 73/427
    See application file for complete search history.

(56) References Cited

U.S. PATENT DOCUMENTS

| | | | | |
|---|---|---|---|---|
| 3,741,656 A | * | 6/1973 | Shapiro | 356/342 |
| 4,247,784 A | * | 1/1981 | Henry | 250/577 |
| 4,810,658 A | * | 3/1989 | Shanks et al. | 436/172 |
| 4,944,922 A | * | 7/1990 | Hayashi | 422/100 |
| 4,952,027 A | * | 8/1990 | Saito et al. | 356/432 |
| 4,979,821 A | * | 12/1990 | Schutt et al. | 356/246 |
| 5,271,902 A | * | 12/1993 | Sakka et al. | 422/100 |
| 5,577,137 A | * | 11/1996 | Groger et al. | 385/12 |
| 5,627,522 A | * | 5/1997 | Walker et al. | 340/618 |
| 5,919,706 A | * | 7/1999 | Tajima | 436/54 |
| 6,079,254 A | * | 6/2000 | Chen et al. | 73/105 |
| 6,100,094 A | * | 8/2000 | Tajima | 436/54 |
| 6,322,752 B1 | | 11/2001 | Siddiqui et al. | |
| 6,375,903 B1 | * | 4/2002 | Cerrina et al. | 422/131 |
| 6,446,022 B1 | * | 9/2002 | Coss et al. | 702/121 |
| 6,623,700 B1 | * | 9/2003 | Horine et al. | 422/100 |
| 6,861,034 B1 | * | 3/2005 | Elrod et al. | 422/100 |
| 2001/0016177 A1 | * | 8/2001 | Pelc et al. | 422/100 |

FOREIGN PATENT DOCUMENTS

| | | |
|---|---|---|
| EP | 0866336 | 9/1998 |
| JP | 10/002904 | 1/1998 |
| JP | 11/083867 | 3/1999 |
| WO | 00/42384 | 7/2000 |

\* cited by examiner

*Primary Examiner*—Brian R. Gordon
(74) *Attorney, Agent, or Firm*—Mattingly & Malur, P.C.

(57) ABSTRACT

In a liquid dispensing apparatus comprising a dispensing probe for sipping and injecting a liquid sample and a dispensing controller for operating the dispensing probe to ascend, descend and rotate, the liquid dispensing apparatus includes a sample moving device for moving a rack holding the liquid sample, a light beam generator, a photosensor for receiving a light beam reflected from a surface of the liquid sample, a computing unit for computing a liquid surface level based on an output signal from the photosensor, and a controller for controlling operations of those components in a supervising way and processing information necessary for the operations. With the liquid dispensing apparatus, precise information of the liquid surface level can be obtained before the start of the dispensing operation.

5 Claims, 5 Drawing Sheets

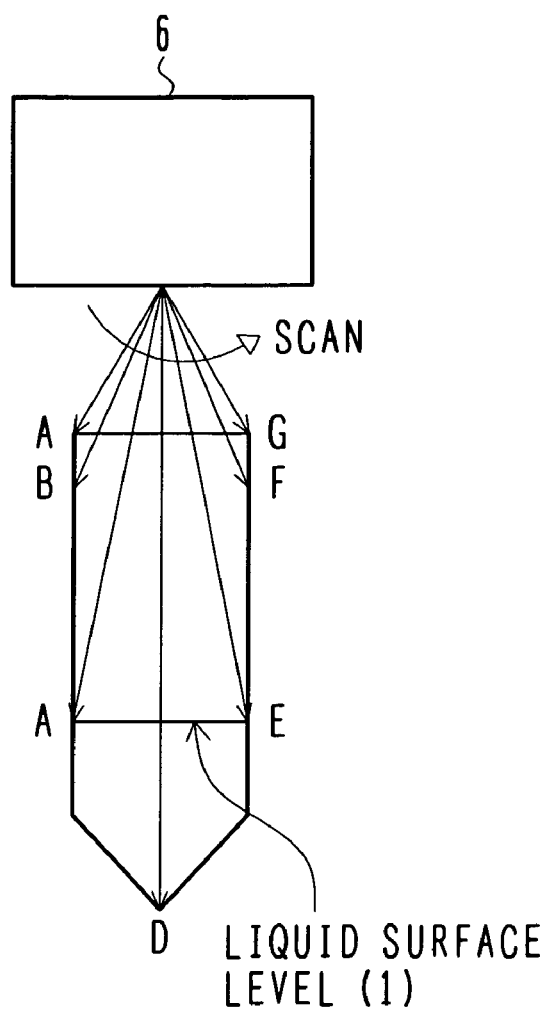
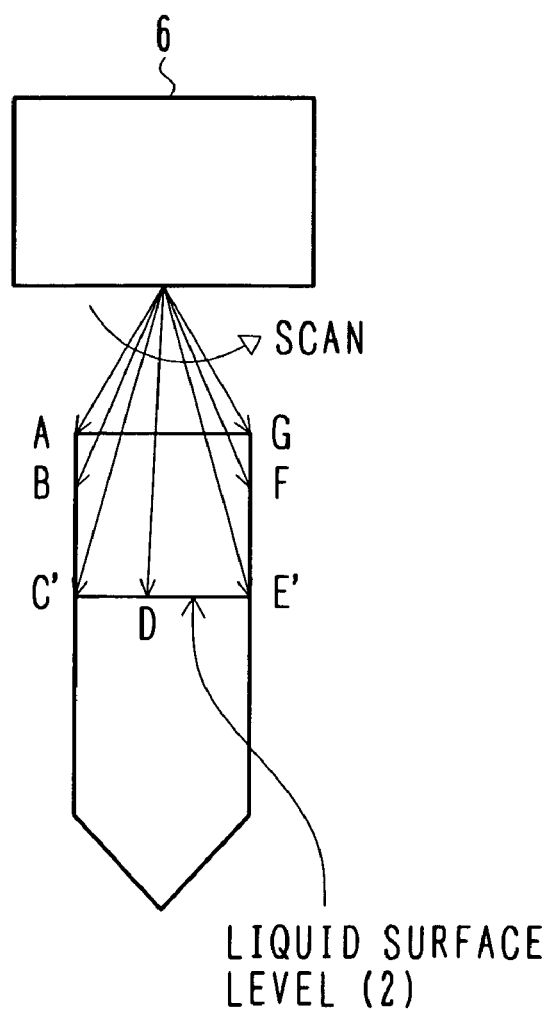
FIG. 4A — LIQUID SURFACE LEVEL (1)
FIG. 4B — LIQUID SURFACE LEVEL (2)

LIQUID DISPENSING APPARATUS, AUTOMATIC ANALYZER USING SAME, AND LIQUID SURFACE DETECTING APPARATUS

BACKGROUND OF THE INVENTION

1. Field of the Invention

The present invention relates to a liquid dispensing apparatus. More particularly, the present invention relates to a liquid dispensing apparatus in which a surface level of a liquid to be dispensed requires to be measured when a dispending probe is descended, an automatic analyzer using the liquid dispensing apparatus, and a liquid surface detecting apparatus.

2. Description of the Related Art

In a liquid dispensing apparatus for sipping a predetermined amount of a liquid in one container and discharging the sipped liquid into another container by using a probe, it is important that, when sipping the liquid, the probe be stopped at a position slightly below a surface level of the liquid to be sipped. If the probe is descended through a stroke to reach a deeper position from the liquid surface level, an increasing risk arises in that the accuracy of the dispensed liquid deteriorate because a larger amount of the liquid attaches to an outer periphery of the probe and the attached liquid drops at the same time as when the sipped liquid is injected into another container. Another possible risk is the so-called carryover that different kinds of liquids mix with each other via the probe.

A technique for precisely detecting the liquid surface is therefore important. In one known liquid dispensing apparatus, electrostatic capacitance between a dispensing probe and a liquid is measured, and a liquid surface is detected by confirming a change of the electrostatic capacitance caused when the dispensing probe contacts the liquid surface. With the known device, however, liquid surface information is obtained only after the dispensing probe has reached a position very close to the liquid surface or has come into contact with the liquid surface. In other words, because the probe enters the liquid without being sufficiently decelerated, there is a possibility that the interface between the probe and the liquid surface may be unstable at the time of sipping the liquid, and hence the dispensing accuracy may deteriorate. If the probe descent speed is slowed down to avoid the above possibility, this causes another problem of a reduction in the dispensing speed.

To overcome the above-described problems, several methods for detecting a liquid surface level in a non-contact manner are proposed. For example, Patent Reference 1; JP,A 10-2904 discloses a method comprising the steps of installing a light source and a photosensor, arranging optical fibers so as to extend from them up to a probe tip, and receiving a light reflected from a liquid surface by the photosensor, thereby detecting a position of the probe tip relative to the liquid surface. Also, Patent Reference 2; JP,A 11-83867 discloses a method comprising the steps of irradiating an ultrasonic wave toward a liquid surface and computing a liquid surface level based on a time that has lapsed until the ultrasonic wave reflected from the liquid surface is received.

SUMMARY OF THE INVENTION

With the method disclosed in Patent Reference 1, whether the illuminated light is reflected from the liquid surface or not is detected by the photosensor. In other words, Patent Reference 1 is just able to determine whether the probe has approached the liquid surface or not, and hence it cannot predict what distance is left until the probe reaches the liquid surface when it continues to descend. Also, the method disclosed in Patent Reference 2 has a difficulty in reducing the spot size of the irradiated ultrasonic wave. Therefore, the irradiated ultrasonic wave is reflected from not only the liquid surface, but also from the edge of a sample cup, thus resulting in a possibility that there may occur a measurement error.

It is an object of the present invention to provide a liquid dispensing apparatus provided with a liquid surface detecting unit capable of detecting a liquid surface level even from a position fairly away from the liquid surface, an automatic analyzer using the liquid dispensing apparatus, and a liquid surface detecting apparatus.

To achieve the above object, the present invention is constructed as follows.

The liquid dispensing apparatus of the present invention comprises a container for containing a liquid; a light beam illuminating unit for illuminating a light beam to a surface of the liquid contained in the container at a predetermined angle other than a direction normal to the liquid surface; a light receiving unit for receiving the light beam reflected from the liquid surface; a dispensing unit provided with a dispensing probe for dispensing the liquid contained in the container; and a control unit for controlling operation of the dispensing probe in accordance with a signal from the light receiving unit which has received the light beam.

When a light is illuminated to a liquid surface in a direction normal to the liquid surface, the light is reflected only in a direction exactly opposed to the direction of incidence of the light. Because the principle of the present invention is based on the fact that the direction in which the light beam illuminated to the liquid surface at the predetermined angle is reflected varies depending on a position in the liquid surface, the advantage of the present invention is not obtained if the light beam is illuminated to the liquid surface in the direction normal to it. Therefore, the incident angle of the illuminated light beam is limited to "a predetermined angle other than a direction normal to the liquid surface". The incident angle of the illuminated light beam is decided depending on the positional relationship among a top edge of the container containing the liquid, the light beam illuminating unit, and the liquid surface. If the incident angle of the illuminated light beam is small relative to the liquid surface, it is difficult to measure the liquid surface when the position of the liquid surface is low. For that reason, a desired incident angle is not smaller than about 60 degrees, but smaller than 90 degrees relative to the liquid surface. In the case of the incident angle being close to 90 degrees, since a displacement of the angle of reflection resulting from a change of the liquid surface position is small and a light receiving device with high accuracy must be used. Accordingly, a preferable range of the incident angle is from about 70 to 80 degrees from the practical point of view.

Also, because of the necessity of precisely detecting the position where the light beam is reflected (or the angle of reflection of the light beam), the light beam used in the present invention is preferably a convergent beam instead of a divergent beam. When a laser beam source, an ordinary halogen lamp or an LED is used as a light source, an emitted light beam is preferably employed after it has been sufficiently converged by an optical lens or the like.

The light receiving unit is preferably a semiconductor photosensor such as a CCD. From the viewpoint of reducing the cost, the light receiving unit is preferably a linear photosensor (i.e., an array of photosensor units arranged in the linear form).

The light beam illuminating unit may include a mechanism for changing an incident angle of the light beam. In this case, the position and angle of the light source itself may be changed. Alternatively, the light beam illuminating unit may be arranged such that the light source is fixed and the radiated light beam is introduced to a reflecting mirror before being illuminated to the liquid surface while an angle of the reflecting mirror is changed.

The liquid surface is always slightly fluctuating due to ambient vibrations, airflows, etc. To eliminate the effect of the fluctuating liquid surface, the signal obtained from the light receiving device is preferably subjected to processing to remove noises by employing the known technique (such as differentiation of the signal).

Moreover, the liquid dispensing apparatus may be combined with the known technique for detecting the liquid surface, i.e., one or both of a liquid surface detecting unit of electrostatic capacitance type detecting the liquid surface based on a change of electrostatic capacitance between the dispensing probe and the liquid, and a liquid surface detecting unit of pressure type ejecting air from a tip of the dispensing probe and measuring a pressure change, to thereby detect the liquid surface. This feature increases the accuracy in detecting the liquid surface.

By employing the liquid dispensing apparatus of the present invention, the liquid surface level can be detected before the start of the dispensing operation. It is hence possible to provide a liquid dispensing apparatus in which a time required for the dispensing operation can be minimized by first quickly descending the dispensing probe to a position slightly above the liquid surface that has been detected, and then slowly descending the probe to enter the liquid while precisely detecting the liquid surface (in combination with, e.g., the liquid surface detecting unit of electrostatic capacitance type), and in which a problem of carryover or the like can be suppressed.

BRIEF DESCRIPTION OF THE DRAWINGS

FIGS. 4A and 4B show examples of light beam illumination angle control in the second embodiment;

DESCRIPTION OF THE PREFERRED EMBODIMENTS

The present invention will be described in detail below in connection with preferred embodiments.

First Embodiment

Figure 1:
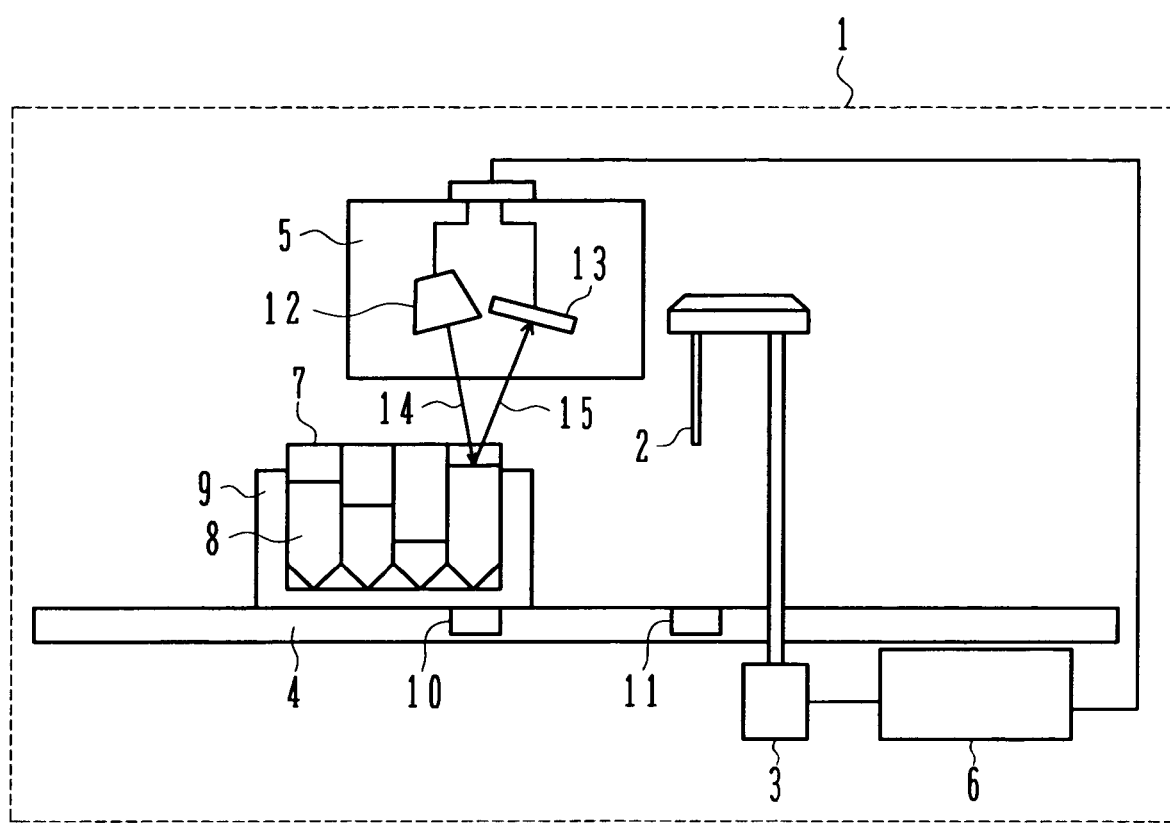
FIG. 1 is a schematic view of a first embodiment of the present invention.

FIG. 1 is a schematic view of a first embodiment of a liquid dispensing apparatus according to the present invention.

Figure 2:
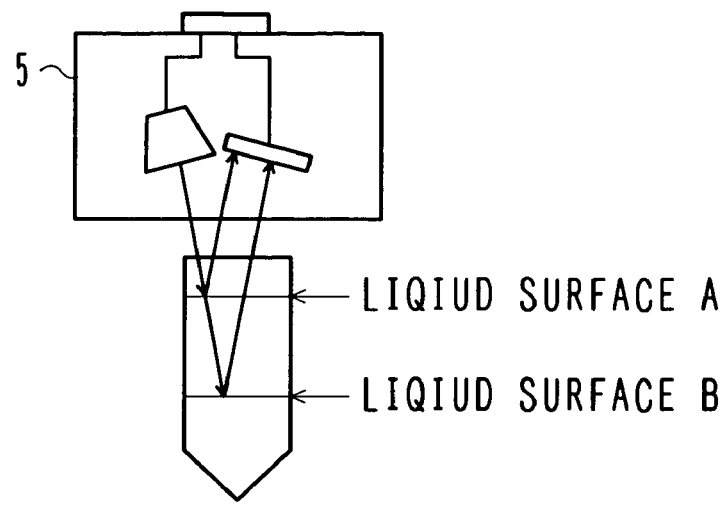
FIG. 2 is a schematic view showing the relationship between a liquid surface level and a focused position of a reflected light beam.

Referring to FIG. 1, a liquid dispensing apparatus 1. comprises a dispensing probe 2, a dispensing controller 3, a sample moving device 4, an optical detection unit 5, and a controller 6. The dispensing probe 2 serves to sip a required amount of a liquid sample 8 from a liquid sample cup 7, and to inject the sipped sample into another container. The dispensing probe 2 is operated to ascend, descend and rotate in accordance with commands from the dispensing controller 3. The sample moving device 4 includes a mechanism for carrying a rack 9, and sensors 10, 11 for detecting a position of the rack 9. The sample moving device 4 is operated in accordance with a command from the controller 6. The sensor 10 has the function of detecting a position where the light beam is to be illuminated, and the sensor 11 has the function of detecting a position where the dispensing is to be performed. The controller 6 controls operations of various components while supervising an overall operation of the liquid dispensing apparatus. The controller 6 includes a processing unit which receives a signal from the optical detection unit 5, executes data processing of the received signal after A/D conversion, and detects a liquid surface level from the processed result. The optical detection unit 5 is connected to the controller 6, and comprises a light beam generator 12 and a photosensor 13. FIG. 2 shows the relationship between a liquid surface level of the liquid sample and a focused position of a reflected light beam. The light beam generator 12 illuminates a light beam 14 toward the liquid sample cup 7 and the liquid sample 8 at a certain angle. The photosensor 13 receives a reflected light beam 15 and generates a voltage depending on the focused position of the reflected light beam 15 on the photosensor 13.

The liquid dispensing apparatus 1 having the above-described construction operates as follows. A set of several liquid sample cups 7 each containing the liquid sample 8 are placed in the rack 9. The rack 9 is moved toward the measurement position by the sample moving device 4. When the sensor 10 detects that the rack 9 has reached the measurement position, the optical detection unit 5 illuminates the light beam. Then, the controller 6 receives data from the photosensor 13 and processes the received data to compute an intensity distribution of the reflected light beam on the photosensor 13, thereby detecting the liquid surface level based on the computed result. At this time, a similar measurement is performed several times per sample, as required. After completing the measurements of all the samples in the rack 9, the sample moving device 4 moves the rack 9 toward the dispensing position and stops the movement of the rack 9 when the sensor 11 detects that the rack 9 has reached the dispensing position. After the stop of the rack 9, the dispensing probe 2 is first quickly descended to a position just above the liquid surface level that has been computed, and then slowly descended to enter the liquid for sipping in accordance with commands from the controller.

Second Embodiment

Figure 3:
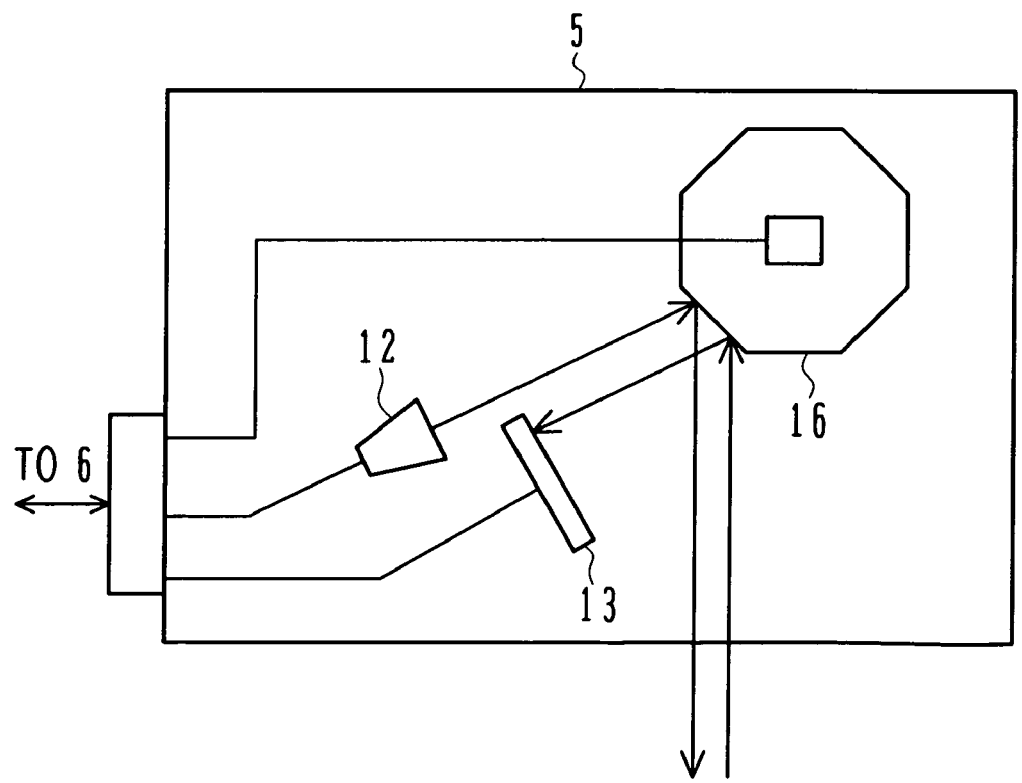
FIG. 3 is a schematic view of an optical detection unit according to a second embodiment.
Figure 5:
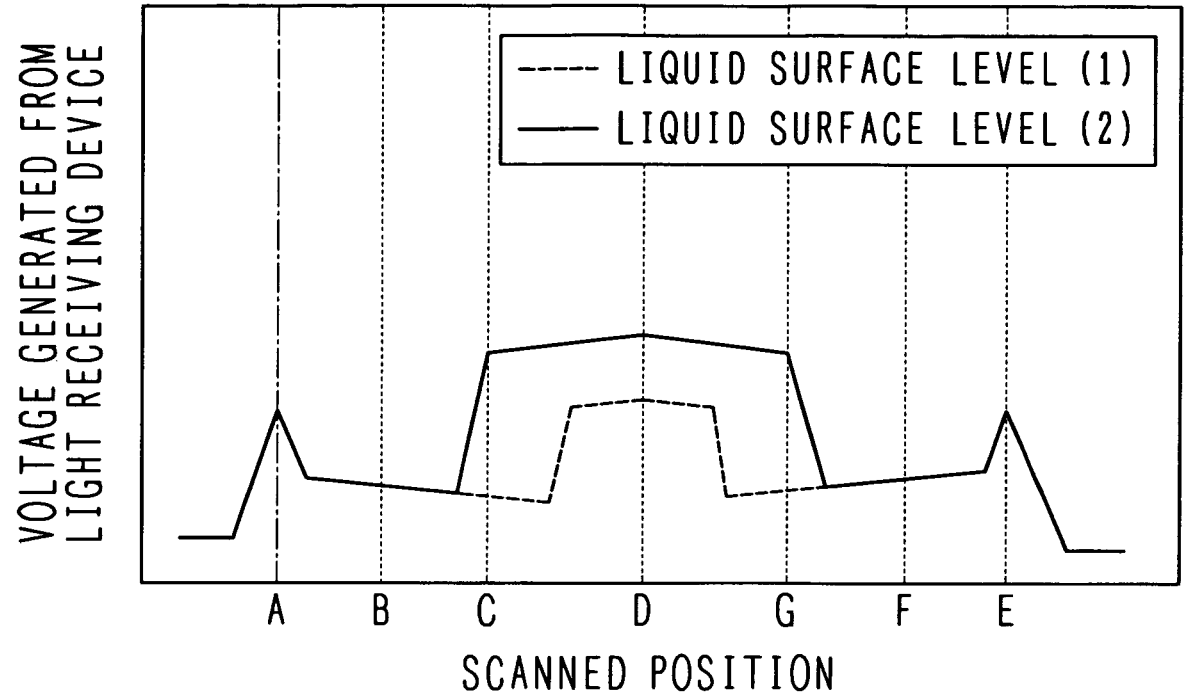
FIG. 5 shows examples of reflected light data in the second embodiment.

FIG. 3 is a schematic view of an improved optical detection unit according to a second embodiment. The optical detection unit 5 includes an illumination angle control mechanism 16 for controlling the angle of the light beam generated from the light beam generator 12, and the controller 6 includes a processing unit to compute the liquid surface level based on information regarding the illuminated light beam angle and the output signal from the photosensor 13. The processing unit correlates the light beam illumination angle with reflected light data at each angle, and processes the reflected light data, thereby computing the liquid surface level. FIGS. 4A and 4B show examples of a control manner for the light beam illumination angle, and FIG. 5 shows examples of the reflected light data obtained in this embodiment.

Furthermore, the dispensing controller 3 may include a memory for storing sets of reflected light data for plural types of liquid sample cups beforehand, and the type of the used liquid sample cup may be identified by comparing the measured reflected light data with the stored data in one of the processing steps.

When there are air bubbles on the liquid sample surface, the reflection condition of the illuminated light beam is possibly disturbed at the interfaces between the liquid sample surface and the air bubbles. In view of that fact, this embodiment may be modified such that the processing unit has the function of differentiating the reflected light data in terms of time and comparing the obtained result with a threshold, to thereby determine the presence of air bubbles.

Third Embodiment

In a third embodiment, the liquid dispensing apparatus 1 includes one liquid surface detecting system of the type detecting electrostatic capacitance or pressure, or two systems of both the types. When the dispensing probe 2 is descended in accordance with the information of the liquid surface level that has been computed before the sipping as described in the first and second embodiments, the liquid surface level can be detected with higher accuracy by detecting the liquid surface level again by using the one or two liquid surface detecting systems in a combined manner.

Fourth Embodiment

A fourth embodiment includes a mechanism capable of moving the optical detection unit 5 or each of the light beam generator 12 and the photosensor 13 relative to the liquid sample 8. When the liquid surface level is detected in accordance with any of the above-described first to third embodiments, it is often required to optimize the position where the optical detection unit 5, etc are installed. In such a case, this embodiment enables the optical detection unit 5 or each of the light beam generator 12 and the photosensor 13 to be moved in the vertical direction or tilted obliquely in accordance with information from the controller 6.

Fifth Embodiment

Figure 6:
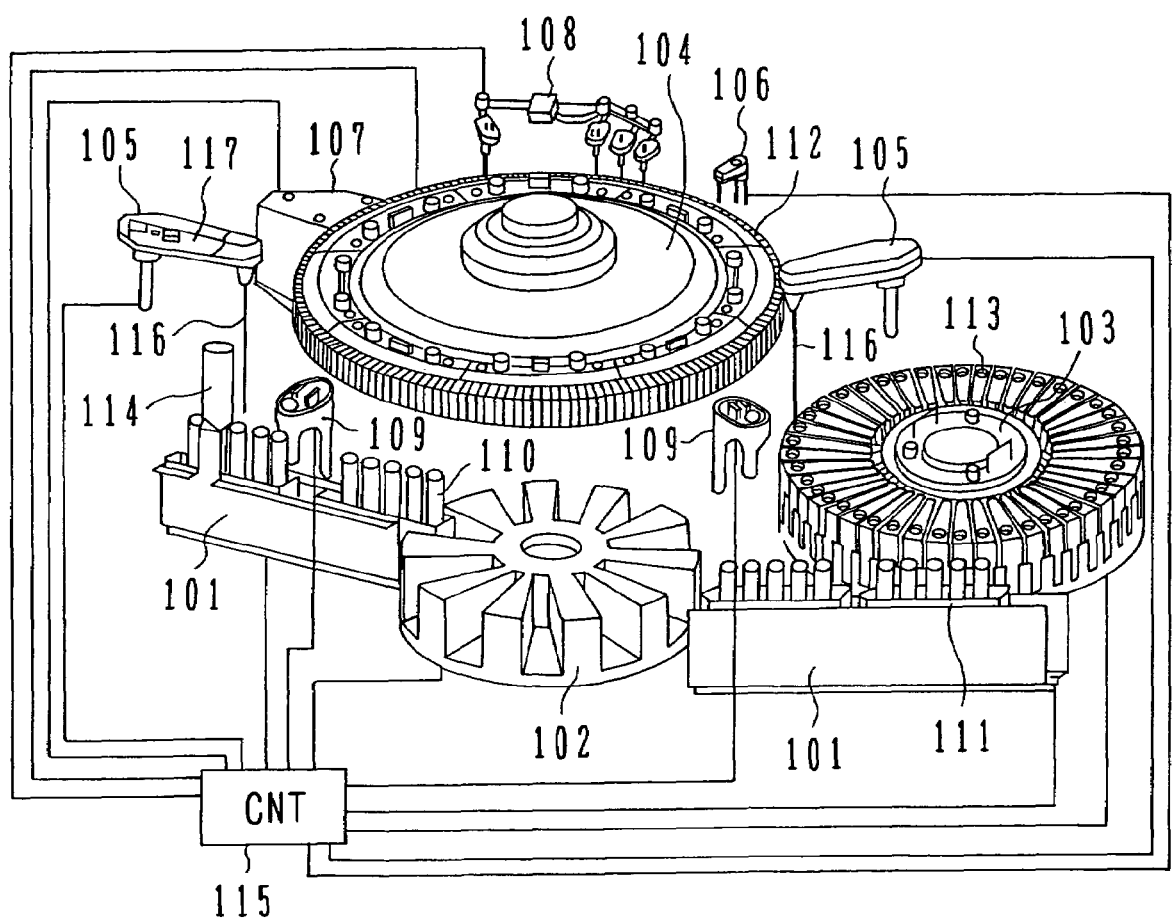
FIG. 6 is a schematic view of a fifth embodiment.

FIG. 6 shows a fifth embodiment in which the optical detection unit according to the present invention is applied to an automatic analyzer.

Referring to FIG. 6, the automatic analyzer comprises transport lines 101, a rotor 102, a reagent disk 103, a reaction disk 104, a dispensing mechanism 105, a stirring mechanism 106, a spectroscope 107, a reaction cell cleaning mechanism 108, a nozzle cleaning mechanism 109, a controller 115, the optical detection unit, and so on.

One transport line 101 is used to carry a sample rack 111 for holding a plurality of sample cups 110, each of which contains a sample, to a position where the dispensing mechanism 105 is able to perform the dispensing operation for distributing a required amount of the sample to a reaction cell 112, whereby a colorimetric analysis utilizing a biochemical reaction takes place in the reaction cell. The transport lines 101 are each connected to the rotor 102 such that the sample rack 111 is transferred from one to another transport line 101 with rotation of the rotor 102.

The reagent disk 103 holds a plurality of reagent bottles 113 each containing a reagent. The reagent disk 103 is rotated to move a reagent, which reacts with a component of the sample to be analyzed, to the position where the dispensing mechanism 105 is able to perform the dispensing operation for distributing the reagent to the reaction cell 112 in amount required for the calorimetric analysis.

The reaction disk 104 holds, on a constant-temperature medium represented by water, the reaction cell 112 containing a reaction liquid, i.e., a mixture of the sample and the reagent, during a period in which the chemical reaction takes place between the component of the sample and the reagent. Also, the reaction disk 104 is rotated to move the reaction cell 112 in a sequential manner to each of respective positions where the spectroscope 107 for the calorimetric analysis, the stirring mechanism 106, the reaction cell cleaning mechanism 108, etc. are operated to execute their functions.

The dispensing mechanism 105 sips the required amounts of the sample and the reagent corresponding to an intended analysis item from the sample cup 110 and the reagent bottle 113, respectively, and then injects the sipped sample and reagent into the reaction cell 112 to perform the colorimetric analysis.

A nozzle 116 provided in the dispensing mechanism 105 is connected to a liquid surface sensor or a pressure sensor, indicated by 117, for detecting the presence of the liquid surface based on a change of electrostatic capacitance or pressure. The nozzle 116 serves to detect the liquid surface level with high accuracy during the dispensing operation.

The stirring mechanism 106 stirs the reaction liquid in the reaction cell 112 to accelerate the reaction between the analysis target component in the sample injected from the sample cup 110 into the reaction cell 112 and the reagent injected from the reagent bottle 113 into the reaction cell 112.

The spectroscope 107 serves to perform the colorimetric analysis of the reaction liquid, which has developed the chemical reaction and has been stirred by the stirring mechanism 106, based on an absorbance measurement.

The reaction cell cleaning mechanism 108 serves to clean the reaction cell 112 by sucking the reaction liquid from the reaction cell 112 for which the colorimetric analysis has completed, and injecting a detergent into it.

The nozzle cleaning mechanism 109 serves to clean the nozzle end of the dispensing mechanism 105, which has been used to dispense the sample and the reagent, so that the remnants will not adversely affect a target to be next analyzed.

The optical detection unit is disposed on the transport line 101 or the rotor 102 to detect the liquid surface level in the sample cup before the rack is moved to the dispensing position.

What is claimed is:

1. A liquid dispensing apparatus comprising:
   a container which contains a liquid;
   a dispensing probe which dispenses said liquid in said container;
   a light beam generator;
   an illumination angle control mechanism which reflects a light beam from said light beam generator toward said container and said liquid in said container, said illumination angle control mechanism changing an illuminating angle of said light beam toward said container and liquid in said container to illuminate said light beam at a plurality of illumination angles to said container and said liquid in said container;
   a photosensor which receives said light beam which is reflected a plurality of times from said container and said liquid in said container;
   a controller which computes a liquid surface level of said liquid in said container on the basis of the plurality of illumination angles of said light beam and output signals received from said photosensor; and a dispensing controller which controls operations of said dispensing probe in accordance with said liquid surface level.

2. A liquid dispensing apparatus according to claim 1, wherein said photosensor is capable of detecting a difference in a light receiving position of said photosensor in at least a one-dimensional direction.

3. A liquid dispensing apparatus according to claim 1, wherein said illumination angle control mechanism includes a mechanism for changing an incident angle of the light beam, and said controller computes the liquid surface level of said liquid in said container based on an incident angle of the light beam and a corresponding output signal received from said photosensor.

4. A liquid dispensing apparatus according to claim 1, further comprising:

a memory which stores sets of reflected light data for plural types of containers beforehand; and container identifying means for identifying the type of said container by comparing the reflected light data stored in said memory with an output signal received from said light receiving means.

5. A liquid dispensing apparatus according to claim 1, which further includes at least one of an electrostatic capacitance liquid surface detecting system and a pressure liquid surface detecting system wherein a liquid surface of said liquid is detected based on at least one of electrostatic capacitance and pressure.

* * * * *